(12) United States Patent
Rioux et al.

(10) Patent No.: US 8,398,624 B2
(45) Date of Patent: *Mar. 19, 2013

(54) SYSTEM AND METHOD FOR PERFORMING ABLATION USING AN EXPANDABLE MEMBER

(75) Inventors: Robert F Rioux, Ashland, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1337 days.

This patent is subject to a terminal disclaimer.

(21) Appl. No.: 12/119,010

(22) Filed: May 12, 2008

(65) Prior Publication Data

US 2009/0054892 A1    Feb. 26, 2009

Related U.S. Application Data

(63) Continuation of application No. 10/768,037, filed on Feb. 2, 2004, now Pat. No. 7,371,231.

(51) Int. Cl.
*A61B 18/18* (2006.01)
*A61B 18/04* (2006.01)

(52) U.S. Cl. ............................................. 606/32; 606/41

(58) Field of Classification Search .............. 606/32–41; 607/96–101
See application file for complete search history.

(56) References Cited

U.S. PATENT DOCUMENTS

| | | | | |
|---|---|---|---|---|
| 4,709,698 A | * | 12/1987 | Johnston et al. | 606/41 |
| 4,799,479 A | * | 1/1989 | Spears | 606/28 |
| 5,003,991 A | * | 4/1991 | Takayama et al. | 607/99 |
| 5,045,056 A | * | 9/1991 | Behl | 607/98 |
| 5,320,634 A | | 6/1994 | Vigil et al. | |
| 5,429,582 A | * | 7/1995 | Williams | 600/2 |
| 5,505,730 A | | 4/1996 | Edwards | |
| 5,827,273 A | * | 10/1998 | Edwards | 606/41 |
| 5,860,974 A | | 1/1999 | Abele | |
| 5,891,136 A | | 4/1999 | McGee et al. | |
| 5,925,038 A | * | 7/1999 | Panescu et al. | 606/41 |
| 5,931,774 A | | 8/1999 | Williams et al. | |
| 6,041,260 A | | 3/2000 | Stern et al. | |
| 6,053,913 A | | 4/2000 | Tu et al. | |
| 6,123,718 A | | 9/2000 | Tu et al. | |
| 6,129,725 A | | 10/2000 | Tu et al. | |
| 6,149,647 A | | 11/2000 | Tu et al. | |

(Continued)

FOREIGN PATENT DOCUMENTS

JP    2000-140118    5/2000
WO    WO 9510326 A1    4/1995

(Continued)

OTHER PUBLICATIONS

Office action from related Japanese application No. 2006-5551065 dated Feb. 22, 2010, in Japanese with English language translation provided by foreign associate, applicant Boston Scientific Limited (14 pages).

(Continued)

*Primary Examiner* — Linda Dvorak
*Assistant Examiner* — Amanda Scott
(74) *Attorney, Agent, or Firm* — Vista IP Law Group LLP

(57) ABSTRACT

An apparatus comprises a catheter, a conductive element and a balloon. The catheter has a lumen. The conductive element is disposed along the catheter. The balloon has an interior in fluid communication with the lumen of the catheter. The balloon is formed of a conductive material conductively coupled to the conductive element. The balloon has a collapsed configuration and an expanded configuration.

13 Claims, 8 Drawing Sheets

U.S. PATENT DOCUMENTS

| | | |
|---|---|---|
| 6,241,727 B1 | 6/2001 | Tu et al. |
| 6,251,109 B1 * | 6/2001 | Hassett et al. ............... 606/45 |
| 6,290,697 B1 | 9/2001 | Tu et al. |
| 6,485,489 B2 * | 11/2002 | Teirstein et al. ............ 606/41 |
| 6,620,159 B2 * | 9/2003 | Hegde ........................ 606/41 |
| 2002/0019627 A1 | 2/2002 | Maguire et al. |

FOREIGN PATENT DOCUMENTS

| | | |
|---|---|---|
| WO | WO 00/56237 A2 | 9/2000 |
| WO | WO 00/67656 A1 | 11/2000 |
| WO | WO 01/87174 A1 | 11/2001 |
| WO | WO 0195820 A1 | 12/2001 |

OTHER PUBLICATIONS

International Search Report for PCT Application No. PCT/US2004/041427, Apr. 18, 2005.

Written Opinion of the International Searching Authority for PCT Application No. PCT/US2004/041427.

* cited by examiner

SYSTEM AND METHOD FOR PERFORMING ABLATION USING AN EXPANDABLE MEMBER

CROSS-REFERENCE TO RELATED APPLICATION

This application is a continuation of U.S. patent application Ser. No. 10/768,037 entitled "System and Method for Performing Ablation Using a Balloon," filed Feb. 2, 2004 (now U.S. Pat. No. 7,371,231), the disclosure of which is hereby incorporated by reference in its entirety.

BACKGROUND

The invention relates generally to systems and methods for performing ablation. More specifically, the invention relates to a system and method for performing ablation using a balloon, for example, in a previously formed tissue cavity.

Various known techniques exist for treating residual tumor tissue following the gross removal of the tumor. Such post-operative treatments include, for example, radiation techniques and brachytherapy techniques.

These post-operative treatments suffer various shortcomings. For example, radiation techniques use common equipment that involve significant logistical challenges. In addition, radiation techniques are costly and time consuming. Radiation techniques typically involve multiple treatments over weeks and sometimes months. In addition, radiation often results in unintended damage to the tissue outside the target zone. In other words, rather than affecting the likely residual tissue, typically near the original tumor location, radiation techniques often adversely affect healthy tissue. Alternative focused-radiation therapy typically involves costly equipment with limited availability.

Standard brachytherapy techniques typically require simultaneous placement of numerous catheters in the tumor and surrounding tissue with individual radioactive sources. Placement of these catheters can be costly, cumbersome and time consuming.

Thus, a need exists for an improved system and method for treating residual tumor tissue following the gross removal of the tumor.

SUMMARY OF THE INVENTION

An apparatus comprises a catheter, a conductive element and a balloon. The catheter has a lumen. The conductive element is disposed along the catheter. The balloon has an interior in fluid communication with the lumen of the catheter. The balloon is formed of a conductive material conductively coupled to the conductive element. The balloon has a collapsed configuration and an expanded configuration.

DETAILED DESCRIPTION

Figure 1:
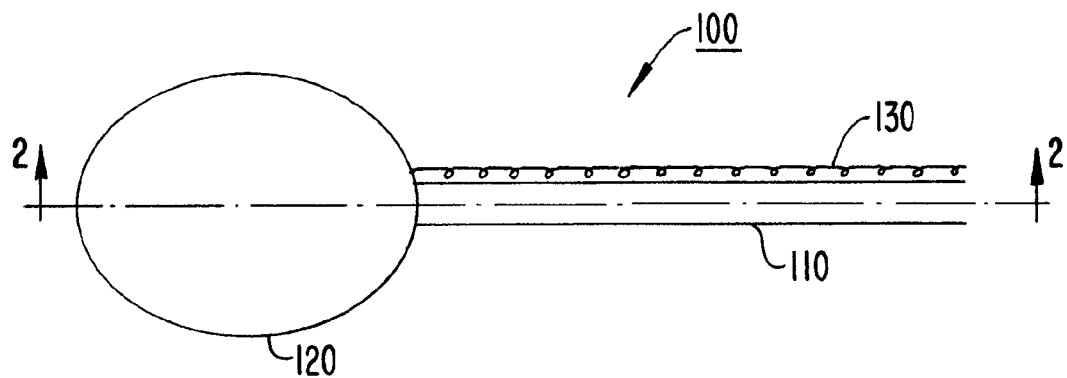
FIG. 1 depicts a side view of a balloon catheter in an expanded configuration, according to an embodiment of the invention.

Once a tumor has been removed, a tissue cavity remains. The tissue surrounding this cavity is the location within the patient where a reoccurrence of the tumor may most likely occur. Consequently, after a tumor has been removed, it is desirable to destroy the surrounding tissue (also referred herein as the "margin tissue"). Various embodiments described herein relate to balloon catheter devices and methods for ablating, for example, the margin tissue associated with a tissue cavity formed by the removal of a tumor.

In one embodiment, an apparatus comprises a catheter, a conductive element and a balloon. The catheter has a lumen. The conductive element is disposed along the catheter. The balloon has an interior in fluid communication with the lumen of the catheter. The balloon is formed of a conductive material conductively coupled to the conductive element. The balloon has a collapsed configuration and an expanded configuration.

The balloon has the collapsed configuration, for example, when the balloon is exterior to a patient's body or being percutaneously disposed into the previously formed tissue cavity. The balloon in the collapsed configuration has a smaller size or volume than when the balloon is in the expanded configuration. The balloon has the expanded configuration, for example, when the balloon is disposed within the previously formed tissue cavity for ablation. In general, the balloon has a range of possible configurations, which include the collapsed configuration (typically at its smallest size or volume) and the expanded configuration corresponding to the size of the tissue cavity.

The balloon is constructed to be electrically conductive, or to have electrically conductive portions. The electrical conductivity can be achieved by forming all or part of the body of the balloon from electrically conductive material (such as for example, a conductive polymer or a non-conductive material that incorporates conductive elements such as metallic particles or other metallic elements) with a conductive layer or coating, such as a conductive ink, or with conductive elements attached to the balloon. In embodiments of the balloon where the conductive material is formed from a conductive polymer, the balloon can be formed, for example, using photolithography techniques. In embodiments of the balloon where the conductive material has a specific shape, the conductive material of the balloon can be formed from, for example, metallic stampings, wires or machined shapes. The term "electrically conductive" is used herein to mean the property of a material or medium permitting flow of electricity through its volume for the conditions to which it is normally subjected. In other words, although all materials and mediums are electrically conductive to some extent, electrically conductive materials or mediums considered herein exclude materials or mediums that are electrically conductive only at levels that are uncharacteristically high for typical ablation devices.

Figure 2:
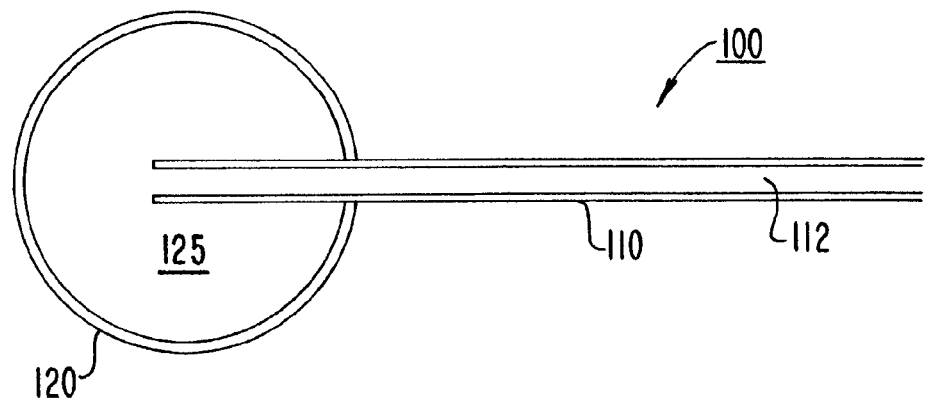
FIG. 2 depicts a cross-sectional view of the balloon catheter of FIG. 1 taken along line 2-2 of FIG. 1.

FIG. 1 depicts a side view of a balloon catheter in an expanded configuration, according to an embodiment of the invention. Balloon catheter 100 includes a catheter 110, a balloon 120 and a conductive element 130 (e.g., a conductive wire covered with insulation). FIG. 2 shows a cross-sectional view of balloon catheter 100 while in the expanded configuration. As shown in FIG. 2, catheter 110 includes a lumen 112 and balloon 120 defines an interior 125.

Figure 3:
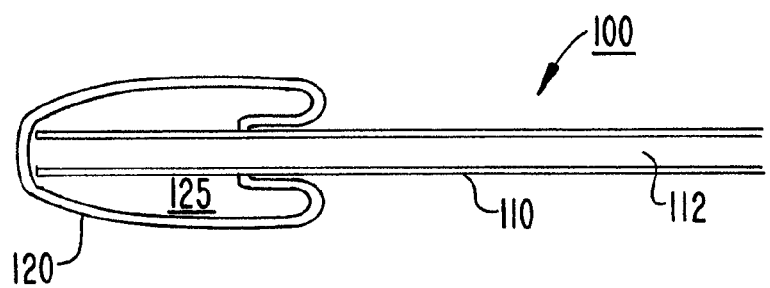
FIG. 3 shows a cross-sectional view of the balloon catheter shown in FIGS. 1 and 2 while in a collapsed configuration.

FIG. 3 shows a cross-sectional view of the balloon catheter shown in FIGS. 1 and 2 while the balloon catheter is in a collapsed configuration. The balloon catheter 100 can be changed from a collapsed configuration to an expanded configuration by introducing a fluid into lumen 112. As the fluid traverses lumen 112, it can then fill the balloon cavity 125 thereby expanding balloon 120 into its expanded configuration. The fluid can be, for example, a liquid such as water or a saline solution, or can be a gas, such as air. Although the conductive element 130 is shown in FIG. 1 as being disposed along and on the catheter 110, in alternative embodiments the conductive element 130 is disposed along the catheter 110 and within the lumen 112.

Balloon 120 can be formed, for example, of a conductive material or of a non-conductive material with conductive material uniformly distributed throughout balloon 120. Such conductive material can be electrically coupled to conductive element 130 thereby allowing energy, such as radiofrequency (RF) energy, to be transferred from conductive element 130 to the conductive material of balloon 120. Such RF energy can be provided by an RF generator (not shown in FIGS. 1 through 3) coupled to conductive element 130. Balloon catheter 100 can operate as a monopolar device where the other pole (not shown) is disposed on the patient.

Figure 4:
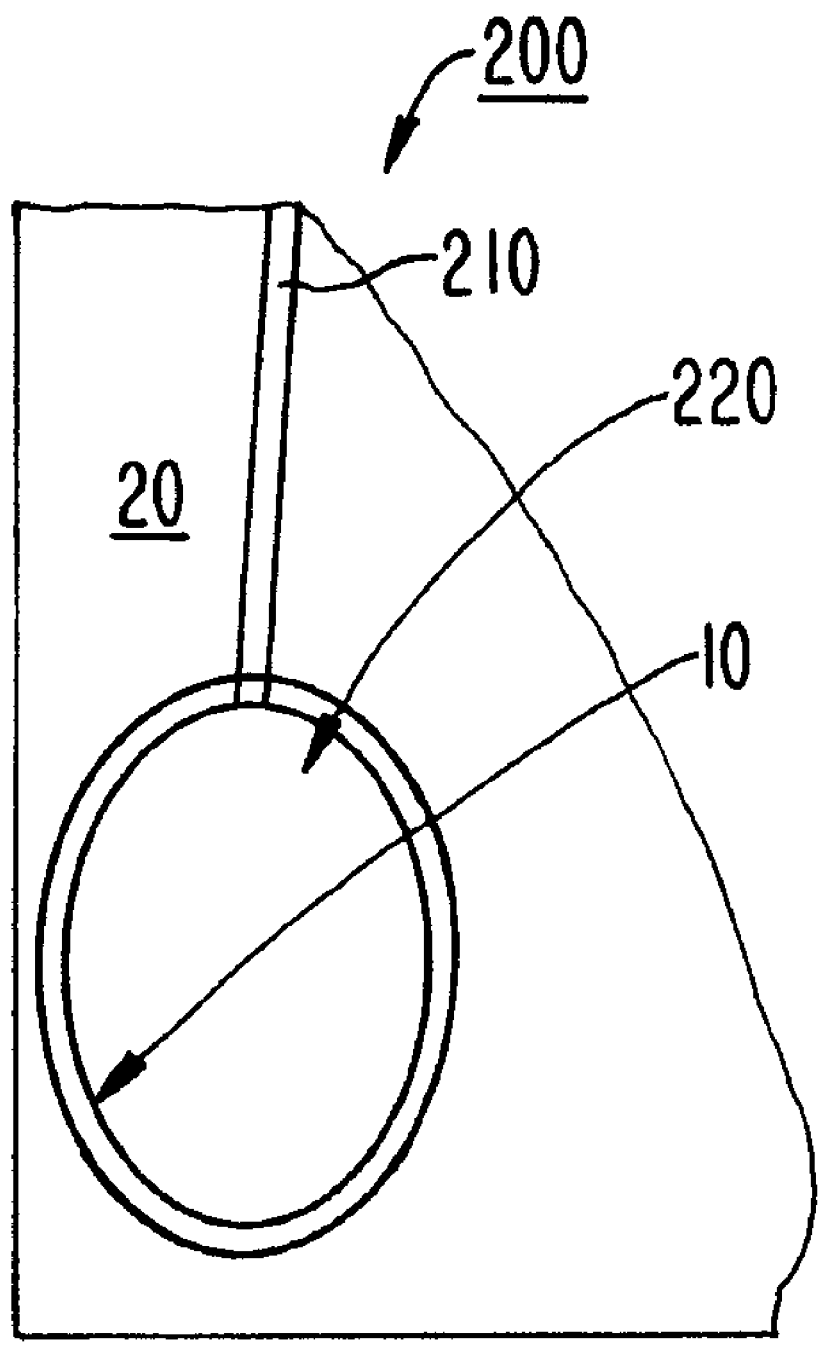
FIG. 4 illustrates a cross-sectional view of the balloon catheter shown in FIGS. 1 and 2 while in the expanded configuration and while disposed within a previously formed tissue cavity.

FIG. 4 illustrates a cross-sectional view of the balloon catheter shown in FIGS. 1 and 2 while in the expanded configuration and while disposed within a previously formed tissue cavity. As shown in FIG. 4, balloon 100 is in the expanded configuration such that balloon 120 expands to fill the previously formed tissue cavity. The previously formed tissue cavity is surrounded by margin tissue 10. As the balloon catheter is activated, the balloon catheter defines a kill zone 20 within which the margin tissue 10 is destroyed through ablation.

Figure 5:
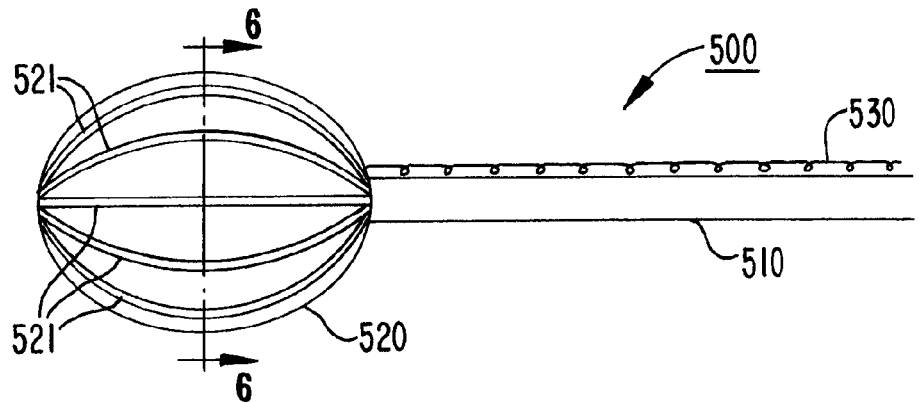
FIG. 5 shows a side view of a balloon catheter according to another embodiment of the invention.
Figure 6:
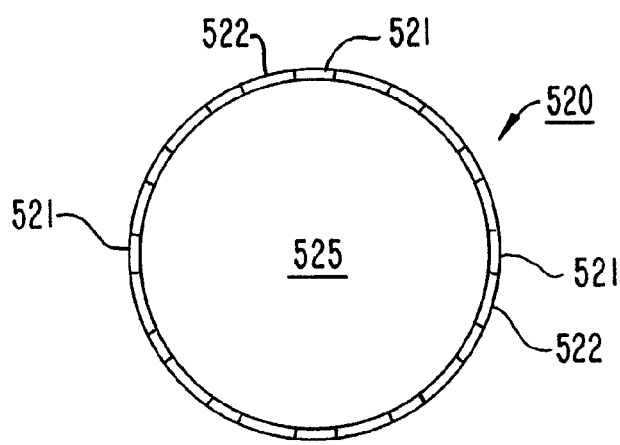
FIG. 6 shows a cross sectional view of the balloon catheter of FIG. 5 taken along line 6-6 of FIG. 5.

FIG. 5 shows a side view of a balloon catheter according to another embodiment of the invention. Balloon catheter 500 includes catheter 510, balloon 520 and conductive element 530. Balloon catheter includes a conductive material integrally formed with balloon 520 such that the conductive material is arranged in paths referred to herein as conductive portions 521. FIG. 6 shows a cross-sectional view of balloon catheter 500 shown in FIG. 5. As FIG. 6 shows, balloon 520 includes conductive portions 521 and non-conductive portions 522. Balloon catheter 520 defines an interior 525. Balloon catheter 500 can operate as a monopolar device where the other pole (not shown) is disposed on the patient.

Figure 7:
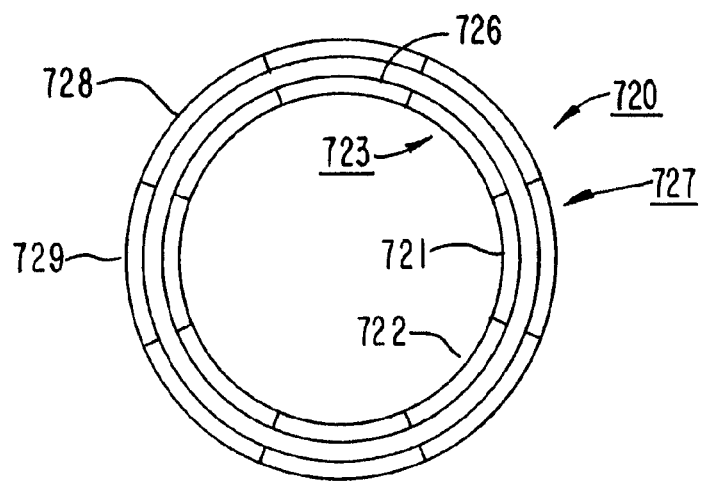
FIG. 7 shows a cross-sectional view of a multi-layer balloon of a balloon catheter while in an expanded configuration, according to another embodiment of the invention.

FIG. 7 shows a cross-sectional view of a multi-layer balloon of a balloon catheter while in an expanded configuration, according to another embodiment of the invention. More particularly, multi-layer balloon 720 includes two concentric balloon portions 723 and 727. Inner balloon 723 includes conductive portions 721 and non-conductive portions 722. Similarly, outer balloon 727 includes conductive portions 728 and non-conductive portions 729. Inner balloon portion 723 and outer balloon portion 727 are arranged such that the conductive portions 721 of inner balloon portion 723 are aligned with the non-conductive portions 729 of outer balloon 727. Similarly, the non-conductive portions 722 of inner balloon 723 are aligned with the conductive portions 728 of outer balloon 727. Disposed between inner balloon layer 723 and outer balloon layer 727 is an insulation layer 726.

Multi-layer balloon 720 can operate as a bipolar device where each balloon portion 723 and 727 are separate poles. More specifically, insulation layer 726 allows conductive layer 721 of inner balloon layer 723 and conductive portion 728 of outer balloon layer 727 to separately receive RF energy and thereby define RF fields between adjacent conductive portions. For example, a given conductive portion 721 of inner balloon portion 723 can act as one pole, and the two adjacent conduction portions 728 of outer balloon portion 727 can act as the other poles. Following this example, an RF field can be established between that conductive portion 721 of inner balloon portion 723 and one of the adjacent conductive portions 728 of outer balloon portion 727, and a separate RF field be established between that conductive portion 721 of inner balloon portion 723 and the remaining adjacent conductive portion 728 of outer balloon portion 727.

Figure 8:
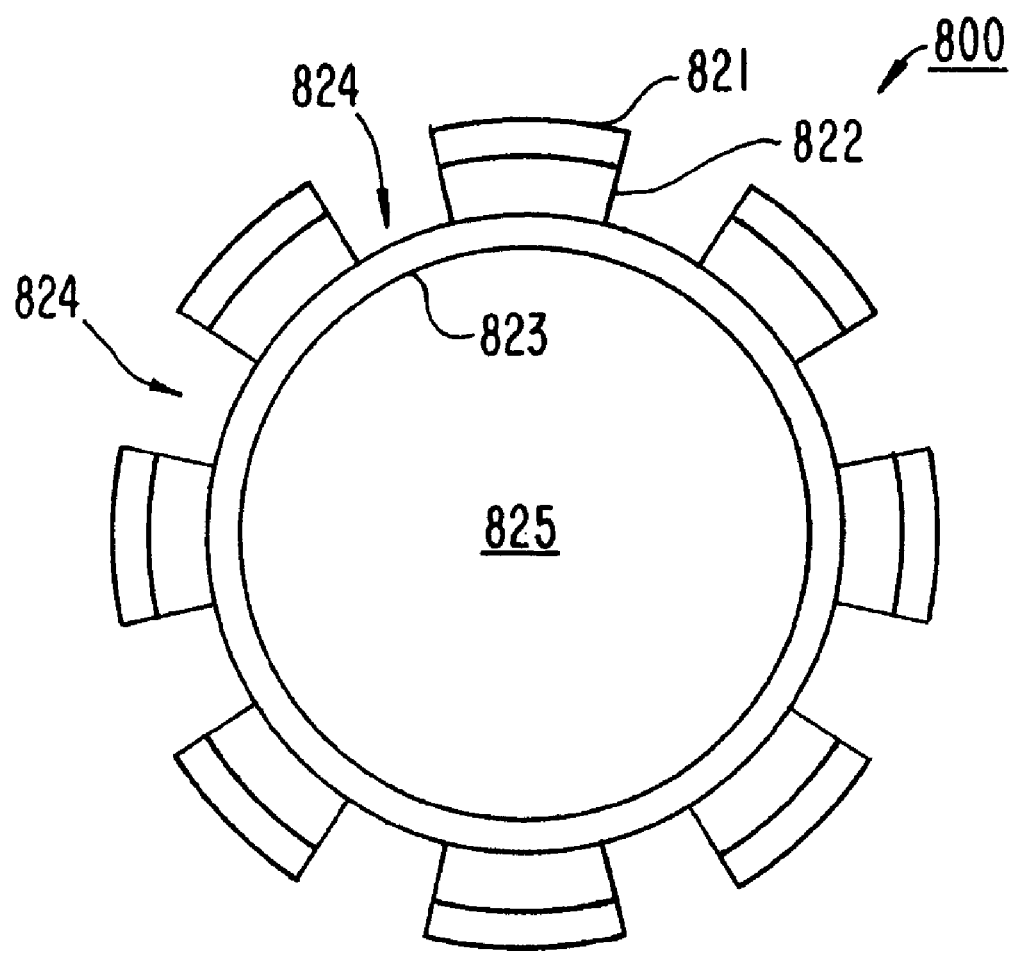
FIG. 8 shows a cross-sectional view of a multi-layer balloon of a balloon catheter while in an expanded configuration, according to yet another embodiment of the invention.

FIG. 8 shows a cross-sectional view of a multi-layer balloon of a balloon catheter while in an expanded configuration, according to yet another embodiment of the invention. Multi-layer balloon 800 includes a conductive layer 823, an insulation layer 822 and a conductive layer 821. Conductive layer 821 and insulation layer 822 each have distinct segments where the one segment of the insulation layer 822 is disposed between the conductive layer 823 and an associated segment of the conductive layer 821. Thus, conductive layer 823 includes portions 824, upon which insulation 822 and 821 are not disposed. Balloon catheter 900 can operate as a bipolar device where conductive layer 823 acts as one pole and conductive layer 821 acts as another pole. Such a bipolar device can produce an RF field between the conductive layers 823 and 821 when energize by an RF generator (not shown in FIG. 8).

Although multi-layer balloon 800 is shown as having no material between adjacent segments of insulation layer 822 and conductive layer 821, in alternative embodiments, an insulation layer can be provided between these adjacent segments of insulation layer and conductive layer. In yet another alternative embodiment, an additional insulation layer can be disposed on at least a portion of the conductive layer 821 and/or conductive layer 823.

Figure 9:
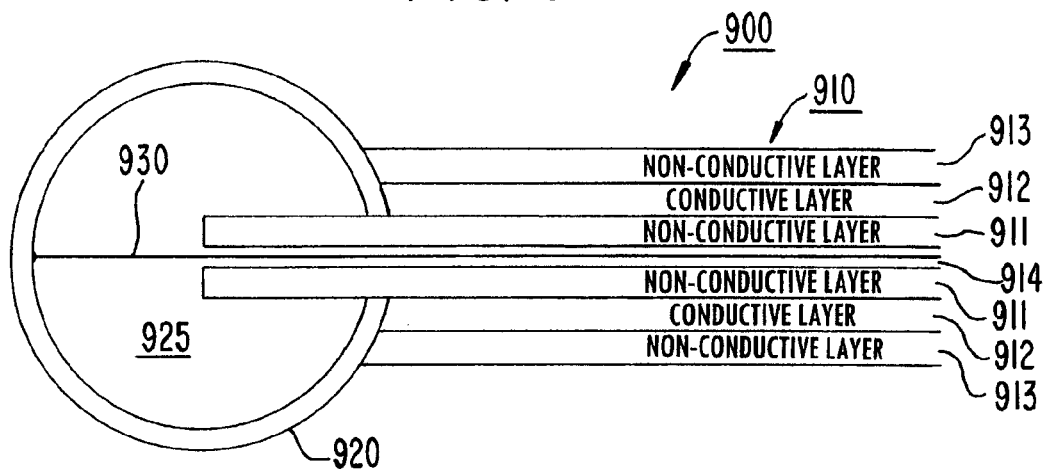
FIG. 9 depicts a cross-sectional view of a balloon catheter having a multi-lumen catheter, according to yet another embodiment of the invention.

FIG. 9 depicts a cross-sectional view of a balloon catheter having a multi-lumen catheter, according to yet another embodiment of the invention. As shown in FIG. 9, balloon catheter 900 includes a catheter 910 and balloon 920. Catheter 910 is a multi-layer catheter including a non-conductive layer 911, a conductive layer 912 and non-conductive layer 913. Non-conductive layer 911 can define lumen 914, which is in fluid communication with the interior 925 of balloon 920. Conductive layer 912 can be electrically coupled to the conductive material of balloon 920 such that energy received from a RF generator (not shown in FIG. 9) can be provided to the conductive material of 920 via conductive layer 912. Conductive layer 912 is thus an alternative to the conductive element 130 shown in FIG. 1 and conductive element 530 shown in FIG. 5.

The balloon catheter 900 shown in FIG. 9 can also include a guide wire 930, which can be disposed within lumen 914 of catheter 910. Guide wire 930 can be used to guide the balloon catheter to an appropriate position within a patient's body such as, for example, a previously formed tissue cavity thereby disposing balloon catheter into a desired location. Although FIG. 9 depicts the balloon catheter 900 in the expanded configuration, guide wire 930 will typically be used while the balloon catheter 900 is in a collapsed configuration.

Figure 10:
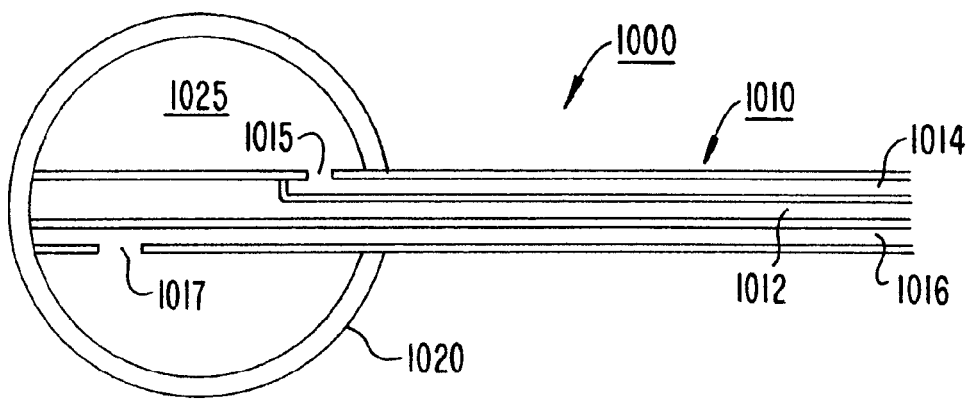
FIG. 10 shows a cross-sectional view of a balloon catheter having a multi-lumen catheter, according to yet another embodiment of the invention.

FIG. 10 shows a cross-sectional view of a balloon catheter having a multi-lumen catheter, according to yet another embodiment of the invention. Balloon catheter 1000 includes a multi-lumen catheter 1010 and a balloon 1020. Multi-lumen catheter 1010 includes lumens 1012, 1014 and 1016. Lumen 1012 can be used for example for a guide wire (not shown in FIG. 10). Lumens 1014 and 1016 can be used to allow the circulation of fluid within interior 1025 of balloon 1020. By controlling the rate at which fluid is introduced into and removed from interior 1025 of balloon 1020, the size of balloon 1020 can be controlled while also allowing the fluid within interior 1025 to circulate. More particularly, by controlling the difference in the rates at which fluid is introduced into and withdrawn from interior 1025, balloon 1020 can be changed between a collapsed configuration and an expanded configuration. Following the example shown in FIG. 10, lumen 1014 can be an input lumen by which fluid can be introduced into interior 1025 via outlet 1015. Lumen 1016 can be an output lumen through which fluid can be withdrawn from interior 1025 through outlet 1017.

This embodiment in which fluid can circulate within interior 1025 also allows a level of control in the manner by which tissue is ablated. More specifically, by allowing the circulation of fluid within interior 1025, the temperature of balloon 1020 can be, for example, reduced. Such a reduction in the temperature of balloon 1020 allows the enhancement of the kill zone of the marginal tissue. Said another way, if the contact temperature of the tissue surrounding balloon 1020 while in an expanded configuration increases too rapidly, the kill zone will be smaller than if the temperature of the marginal tissue is increased at a slower rate. This allows a larger kill zone than would otherwise be the case. Thus, by controlling the circulation of fluid, the temperature of balloon 1020 and therefore the temperature of the surrounding marginal tissue can be controlled thereby allowing the selection of a desired kill zone. Alternatively, the temperature of balloon 120 can be increased, providing a thermal ablation mechanism for necrosis of the margin tissue in addition to the RF ablation mechanism.

Figure 11:
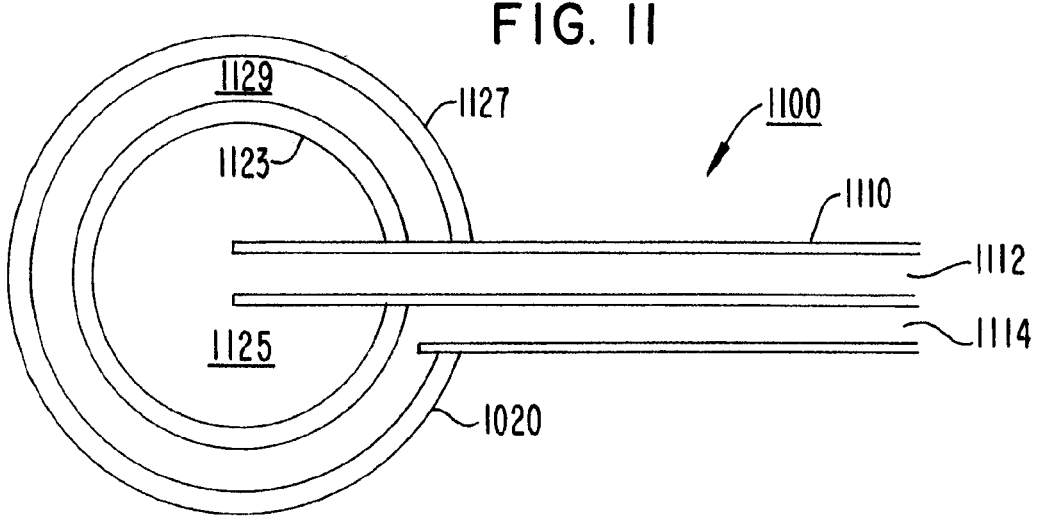
FIG. 11 illustrates a cross-sectional view of a balloon catheter having multiple concentric balloons, according to an embodiment of the invention.

FIG. 11 illustrates a cross-sectional view of a balloon catheter having multiple concentric balloons, according to an embodiment of the invention. Balloon catheter 1100 includes multi-lumen catheter 1110 and multi-layer balloon 1120. Multi-lumen catheter 1110 includes lumen 1112 and lumen 1114. Multi-layer balloon 1120 includes an inner balloon 1123 and an outer balloon 1127. Inner balloon 1123 defines an interior 1125. Interior 1129 is defined as the annular space between inner balloon 1123 and outer balloon 1127. Lumen 1112 of multi-lumen catheter 1110 is in fluid communication with interior 1125 of inner balloon 1123. Similarly, lumen 1114 of multi-lumen catheter 1110 is in fluid communication with interior 1129 of outer balloon 1127. Inner balloon 1123 and outer balloon 1127 can each be formed from a conductive material.

Figure 12:
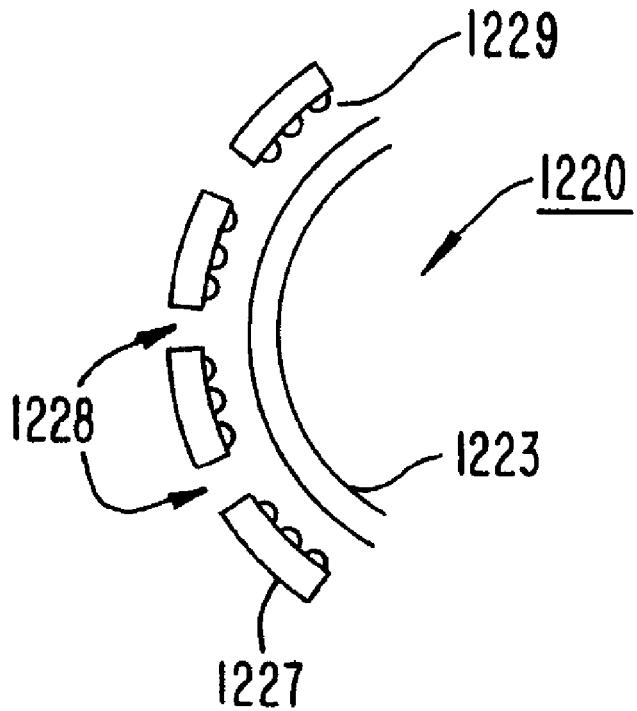
FIG. 12 depicts a partial cross-sectional view of a balloon catheter having multiple concentric balloons, according to another embodiment of the invention.

FIG. 12 depicts a partial cross-sectional view of a balloon catheter having multiple concentric balloons, according to another embodiment of the invention. As shown in FIG. 12, balloon 1220 includes an inner balloon 1223 and outer balloon 1227. Balloon 1220 can be connected to a multi-lumen catheter (not shown in FIG. 12) similar to multi-lumen catheter 1110 shown in FIG. 11. Outer balloon 1227 includes a set of openings 1228 through which fluid can pass. In addition, outer balloon 1227 includes an irregular surface 1229, which provides separation between outer balloon 1227 and inner balloon 1223. This separation allows fluid to better pass between the inner balloon 1223 and outer balloon 1227, and exit the various openings 1228. FIG. 12 is not necessarily shown to scale and, consequently, the openings 1228 can be much smaller, thereby allowing the fluid to pass through the openings 1228 at a lower rate.

The fluid exiting openings 1228 can provide enhanced conductivity to the margin tissue surrounding balloon 1220. By providing enhanced conductivity, the ablation process can be modified. For example, when a fluid having conductivity greater than the margin tissue exits openings 1228, the margin tissue with the fluid has a greater conductivity than would be the case without the fluid. As a consequence, a greater amount of tissue can be ablated. In other words, tissue can be ablation to a greater depth (i.e., a greater distance from the balloon) because a fluid being released into the margin produces an increased conductivity.

The fluid can be any type of fluid that provides increased conductivity. For example, the fluid can be a saline solution. Alternatively, the fluid can be a solution having ferric materials such as those described in U.S. patent application Ser. No. 10/665,110, filed on Sep. 16, 2003, now U.S. Pat. No. 6,961,620, which is incorporated herein by reference. Such a solution can have, for example, ferric particles with a size of 1-100 microns in diameter.

Figure 13:
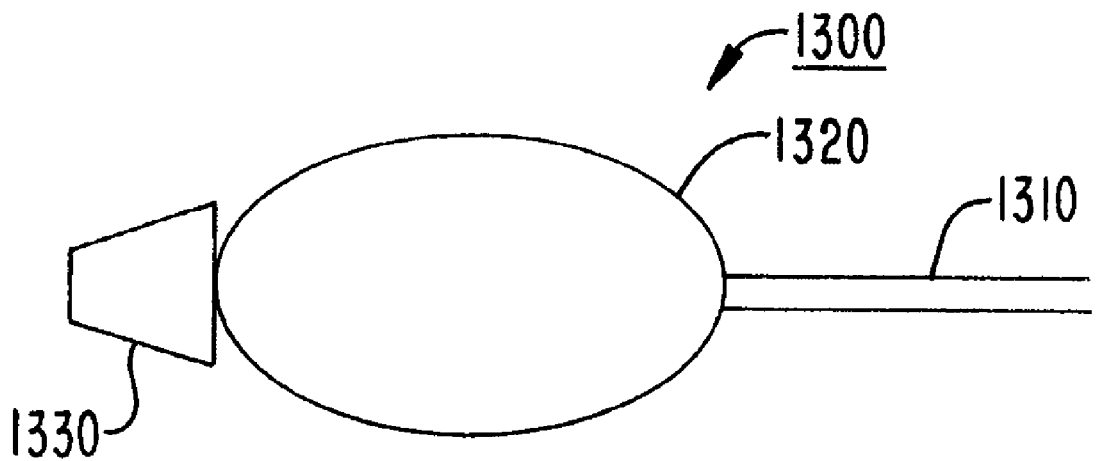
FIG. 13 depicts a side view of a balloon catheter having an atraumatic tip, according to an embodiment of the invention.

FIG. 13 depicts a side view of a balloon catheter having an atraumatic tip, according to an embodiment of the invention. As shown in FIG. 32, balloon catheter 1300 includes catheter 1310, balloon 1320, and atraumatic tip 1350. Atraumatic tip 1350 can provide a blunt end to the balloon catheter 1300. Such a blunt end avoids the creation of any further punctures or holes within the tissue of the patient while the balloon catheter is in the collapsed configuration and moved within the patient. Although shown in connection with balloon catheter 1300, an atraumatic tip can be combined with any appropriate balloon catheter such as the above-described embodiments.

Figure 14:
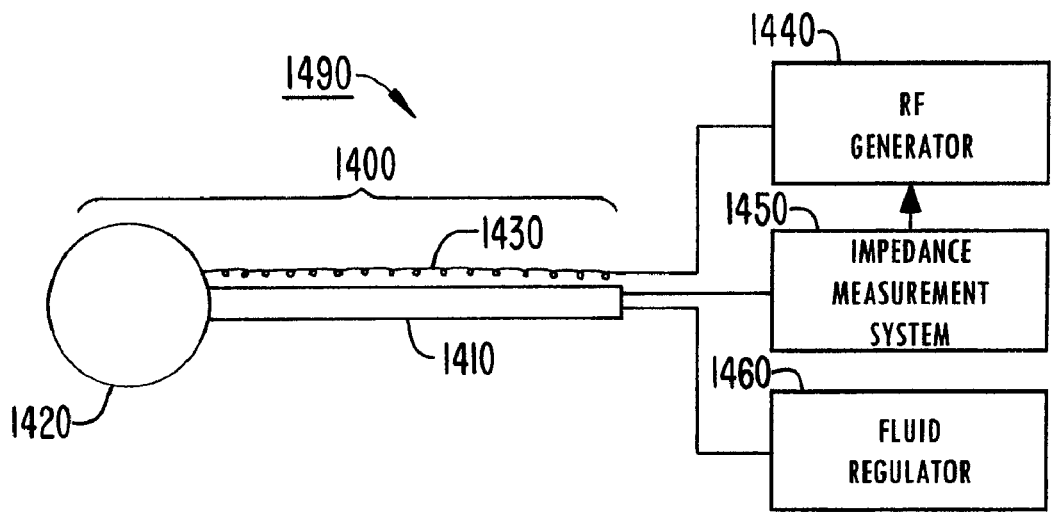
FIG. 14 depicts a block diagram of an ablation system having a balloon catheter, according to an embodiment of the invention.

FIG. 14 depicts a block diagram of an ablation system having a balloon catheter, according to an embodiment of the invention. As shown in FIG. 14, balloon catheter system 1490 includes balloon catheter 1400, RF generator 1440, impedance measurement system 1450 and fluid regulator 1460. Balloon catheter 1400 includes a catheter 1410, a balloon 1420 and a conductive element 1430. Although RF generator 1440, impedance measurement system 1450 and fluid regulator 1460 are shown in FIG. 14 in connection with balloon catheter 1300, they can be used with any of the balloon catheters described above. In addition, impedance measurement system 1450 and fluid regulator 1460 are optional for any of the embodiments described herein.

RF generator 1440 is electrically coupled to conductive element 1430, which is electrically coupled to a conductive material of balloon 1420. Impedance measurement system 1450 can include a sensor (not shown in FIG. 14) disposed on an exterior balloon 1420. Such a sensor can allow the measurement of the impedance of the tissue proximate to the exterior of balloon 1420. The impedance of the tissue proximate to the exterior of balloon 1420 provides an indication of the extent to which that tissue is destroyed through the ablation process. Based on the impedance measurement of the tissue proximate to the exterior of balloon 1420, impedance measurement system 1450 can provide a signal to RF generator 1440. RF generator 1440 can control the amplitude, frequency, and/or power of the RF energy provided to the conductive material of balloon 1320 based on the signal received from impedance measurement system 1450. In this manner, the ablation process can be monitored and controlled.

Fluid regulator 1360 can control the flow of fluid to the balloon 1420. For example, when balloon 1420 includes an outer balloon portion having openings (similar to the outer balloon portion 1227 shown in FIG. 12), fluid regulator 1360 can control the rate at which fluid exits the opening and is introduced to the margin tissue. For another example, when catheter 1410 is a multi-lumen catheter (similar to the multi-lumen catheter shown in FIG. 10), fluid regulator 1360 can control the rate at which fluid circulates within the interior of the balloon 1420.

Figure 15:
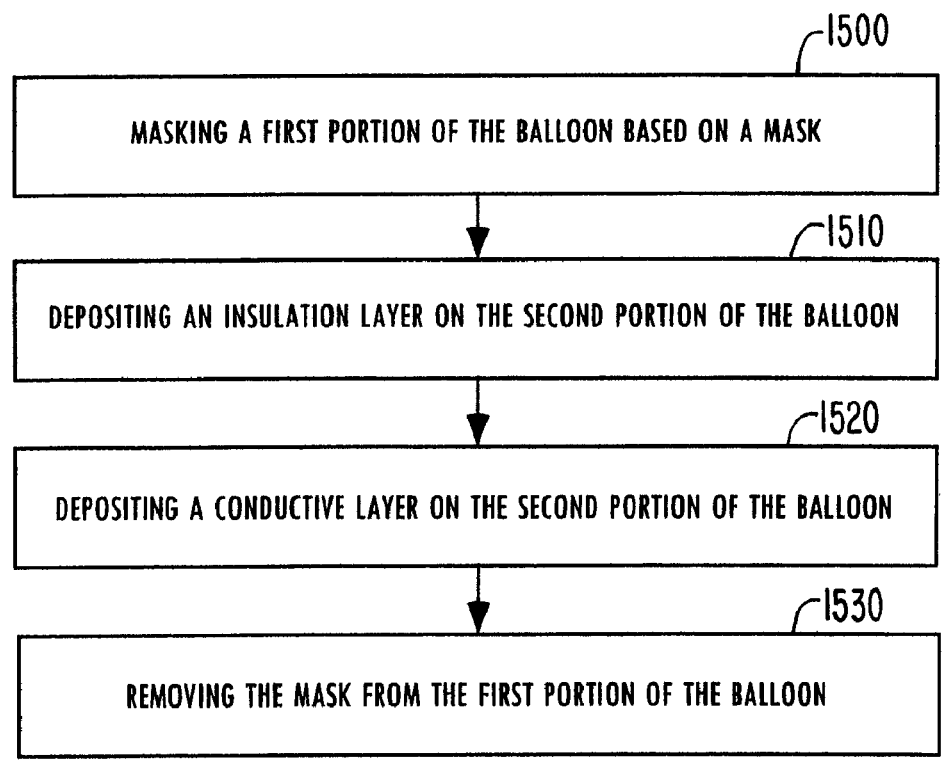
FIG. 15 is a flow chart illustrating a method for making a balloon according to an embodiment of the invention.

FIG. 15 depicts a flowchart for making an ablation balloon, according to an embodiment of the invention. This process described in reference to FIG. 15 is similar to photolithography techniques used in the construction of integrated circuits. Although FIG. 15 describes a process for making many types of ablation balloons, for illustrative purposes FIG. 15 will be described in reference to the balloon shown in FIG. 8 having a first conductive layer, segments of an insulation layer and segments of a second conductive layer.

At step 1500, a first portion of the balloon is masked based on a mask. Following the example of FIG. 8, the shape of the mask and the first portion of the balloon corresponds to the portions 824 of conductive layer 823 of balloon 820. At step 1510, an insulation layer on a second portion of the balloon is deposited. In other words, the insulation layer is disposed on the balloon excluding the masked portions of the balloon. At step 1520, a conductive layer on the second portion of the balloon is deposited. Following the example of FIG. 8, the conductive layer 821 is disposed on the insulation layer 822 of balloon. At step 1530, the mask is removed form the first portion of the balloon. As a result, the first portion of the balloon is exposed as such portions 824 of conductive layer 823 of balloon 800 shown in FIG. 8.

In alternative embodiments, a second insulation layer (not shown in FIG. 8) can be deposited before the mask is removed. Once the mask is removed, the conductive layer will be disposed between the first insulation layer and the second insulation layer. Such a second insulation layer can provide a protective layer over the conductive layer.

In another alternative embodiment, a second insulation layer (not shown in FIG. 8) can be deposited on the first portion and the second portion of the balloon after the masked has been removed. Thus, once the mask is removed, the second insulation layer will be disposed on the conductive layer for the second portion of the balloon and on the first portion of the balloon. Such a second insulation layer can provide a protective layer over the entire balloon.

In one alternative embodiment, the balloon catheter can be used in combination with a radiation therapy device. For example, a radiation therapy device having a balloon-like structure inflated with a radioactive fluid is in U.S. Pat. No. 6,083,148 to Williams, which is incorporated herein by reference. Such radiation therapy device is understood to operate more effectively when the balloon-like structure of the radiation therapy device has a more spherical shape in its expanded configuration. Accordingly, it is desirable for the tissue cavity formed by the removal of a tumor to have a more spherical shape.

An embodiment of the balloon catheter can be used to modify the shape of the tissue cavity formed by the removal of a tumor into a more spherical shape before use of a radiation therapy device. More specifically, the balloon catheter disposed within the tissue cavity can be activated to ablation the surrounding tissue thereby modifying the shape of the tissue cavity to a substantially spherical shape. The balloon catheter can be removed and the radiation therapy device can be inserted into the modified tissue cavity. The radiation therapy device can then apply the radiation therapy.

Although some embodiments of the invention have been described above, for example, in connection with ablating margin tissue after a tumor has been removed, some embodiments can be used in other applications. For such other applications, the balloon can have an alternative shape and structure as may be appropriate for that application. In other words, the particular shape and structure of the balloon can be selected to match the particular anatomy associated with a given application. The various possible balloon structures include, for example, configurations where the balloon is compliant and configurations where the balloon has enough rigidity that the balloon takes on a predefined shape when expanded. Alternatively, possible balloon structures include, for example, configurations where the RF electrodes ablate surrounding tissue via direct contact, and configurations where the RF electrodes heat the fluid within the balloon and the tissue is ablated by the heated balloon. These various alternative applications and structures are discussed below.

In one embodiment, for example, a balloon catheter can be used to treat prostatitis. For such an application, the balloon catheter can be inserted transurethrally and, when in the expanded configuration, the balloon can have an hour-glass shape to provide an improved positioning of the balloon about the prostate lobes. Once positioned and disposed within the expanded configuration, the RF electrodes can be electrically activated to an appropriate level to heat via direct contact. Alternatively, the RF electrodes can be electrically activated to an appropriate level to heat the fluid within the balloon such that the heated balloon can ablate the prostate lobes. Such an embodiment can also be used to treat prostate cancer.

In another embodiment, a balloon catheter can be used for uterine ablation. For such an application, the balloon in an expanded configuration can have a compliant structure that conforms to the shape of the uterine when the balloon is filled with a fluid. In other words, the balloon can be positioned in the uterine cavity transvaginally, inflated into the expanded configuration by filling the balloon with a fluid and then the RF electrodes can be electrically activated to ablate the endometrial lining of the uterus. As discussed above, in an alternative, the RF electrodes can be electrically activated to an appropriate level to heat the fluid within the balloon such that the heated balloon can ablate the endometrial lining of the uterus.

Figure 16:
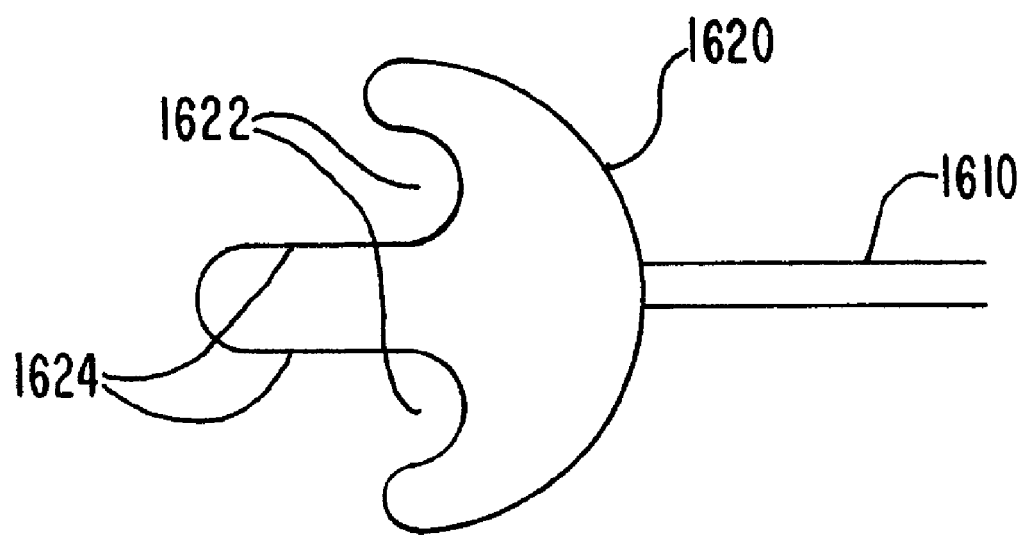
FIG. 16 shows a cross-sectional view of a balloon catheter in an expanded configuration, according to another embodiment of the invention.

In yet another embodiment, the balloon catheter can be used to treat cervical cancer. For such an application, the balloon in an expanded configuration can have a compliant structure in a mushroom-like shape. FIG. 16 shows a cross-sectional view of a balloon catheter in an expanded configuration, according to another embodiment of the invention.

As shown in FIG. 16, balloon catheter 1600 includes catheter 1610 and balloon 1620. Balloon 1620 has a compliant structure that when in an expanded configuration has a mushroom-like shape. Balloon 1620 includes balloon portions 1622 and balloon portion 1624, which are suitable for placement within and surrounding the cervix. More specifically, balloon portion 1624 can be disposed within and through the os; balloon portions 1622 can be disposed about and envelope the cervix. Balloon catheter 1600 can be dimensioned, for example, as a 5 to 7 French distal balloon shape by 3 cm that expands to a concave portion approximately 4 to 6 cm in diameter.

Similar to the discussion above, once positioned, the balloon here can be inflated into the expanded configuration by filling the balloon with a fluid and then the RF electrodes can be electrically activated to ablate the endometrial lining of the uterus. Alternatively, the RF electrodes can be electrically activated to an appropriate level to heat the fluid within the balloon such that the heated balloon can ablate the cervix.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

What is claimed is:

1. An apparatus, comprising
    a catheter defining a first lumen and a second lumen;
    a conductive element disposed along the catheter;
    a first expandable member having an interior in fluid communication with the first lumen of the catheter; and
    a second expandable member having an interior in fluid communication with the second lumen of the catheter;
    each of the first expandable member and second expandable member having respective conductive portions and non-conductive portions, the first expandable member comprising an inner balloon, and the second expandable member comprising an outer balloon, the inner and outer balloons being arranged such that the conductive portions of the inner balloon are aligned with the non-conductive portions of the outer balloon, and the non-conductive portions of the inner balloon are aligned with the conductive portions of the outer balloon.

2. The apparatus of claim 1, further comprising: an insulation layer disposed between the first expandable member and the second expandable member.

3. The apparatus of claim 1, the apparatus comprising a bi-polar tissue ablation device, wherein one or more conductive portions of the second expandable member are coupled to a first pole of the device, and one or more conductive portions of the first expandable member are coupled to a second pole of the device.

4. The apparatus of claim 1, wherein the second expandable member in the expanded configuration has a size associated with a previously-formed tissue cavity.

5. The apparatus of claim 1, wherein the first expandable member and the second expandable member are disposed concentrically.

6. A method, comprising:
    percutaneously disposing at least a portion of a catheter while in a collapsed configuration into a tissue cavity previously-formed by removal of a tissue mass, the portion of the catheter including a first expandable member disposed within a second expandable member, at least a portion of the first expandable member or the second expandable member being formed of a conductive material to define a conductive portion;
    expanding each of the first expandable member and the second expandable member into an expanded configuration, the second expandable member in the expanded configuration having a shape associated with a shape of the previously-formed tissue cavity; and
    applying a radio-frequency signal to the conductive portion of the first expandable member or the second expandable member.

7. The method of claim 6, wherein the expanding includes disposing a fluid within the first expandable member having a temperature less than a temperature of the conductive portion of the first expandable member.

8. The method of claim 6, wherein the second expandable member is fluid permeable, the expanding includes disposing a fluid into the second expandable member such that at least a portion of the fluid is perfused through the second expandable member and into the tissue cavity.

9. The method of claim 6, wherein the second expandable member is fluid permeable, the method further comprising:
    measuring an impedance associated with the tissue cavity,
    the expanding includes providing a fluid within the second expandable member based on the impedance associated with the tissue cavity.

10. The method of claim 6, the applying including modifying the shape of the previously-formed tissue cavity to produce a modified tissue cavity having a substantially spherical shape, the method further comprising:
    removing the portion of the catheter from the modified tissue cavity;
    inserting a radiation therapy device into the modified tissue cavity; and
    performing radiation therapy based on the radiation therapy device.

11. The method of claim 6, wherein the applying includes applying the radio-frequency signal to the conductive portion of the first expandable member or the second expandable member such that heat from the conductive portion of the first expandable member or the second expandable member ablates at least a portion of a margin tissue associated with the tissue cavity.

12. A bi-polar tissue ablation device, comprising:
    a catheter defining a lumen; and
    an expandable member coupled to a distal end of the catheter, and having an interior in fluid communication with the lumen of the catheter, the expandable member comprising a first conductive layer, an insulation layer, and a second conductive layer, the second conductive layer and the insulation layer each having distinct segments in which one segment of the insulation layer is disposed between the first conductive layer and an associated segment of the second conductive layer, the first conductive layer including portions upon which the respective insulation layer and second conductive layer are not disposed.

13. The bi-polar device of claim 12, wherein the first conductive layer acts as one pole, and second conductive layer acts as another pole.

* * * * *